US012779203B2

(12) United States Patent
Curran et al.

(10) Patent No.: US 12,779,203 B2
(45) Date of Patent: Nov. 3, 2026

(54) ESTIMATING CONTRACTILE RESERVE USING A MECHANICAL CIRCULATORY SUPPORT DEVICE

(71) Applicants: Abiomed, Inc., Danvers, MA (US); Massachusetts Institute of Technology, Cambridge, MA (US)

(72) Inventors: Jerald Curran, Danvers, MA (US); Steven Keller, Danvers, MA (US); Elazer Edelman, Danvers, MA (US); Ahmad El Katerji, Danvers, MA (US)

(73) Assignees: Abiomed, Inc., Danvers, MA (US); Massachusetts Institute of Technology, Cambridge, MA (US)

( * ) Notice: Subject to any disclaimer, the term of this patent is extended or adjusted under 35 U.S.C. 154(b) by 374 days.

(21) Appl. No.: 18/533,443

(22) Filed: Dec. 8, 2023

(65) Prior Publication Data

US 2024/0189573 A1 Jun. 13, 2024

Related U.S. Application Data

(60) Provisional application No. 63/431,208, filed on Dec. 8, 2022.

(51) Int. Cl.

*A61M 60/523* (2021.01)
*A61M 60/13* (2021.01)
(Continued)

(52) U.S. Cl.

CPC .......... *A61M 60/523* (2021.01); *A61M 60/13* (2021.01); *A61M 60/17* (2021.01);
(Continued)

(58) Field of Classification Search

None
See application file for complete search history.

(56) References Cited

U.S. PATENT DOCUMENTS 11,357,968 B2 * 6/2022 El Katerji .......... A61B 5/02007
2014/0288442 A1 * 9/2014 Bombardini .......... A61B 5/318 600/513
(Continued)

FOREIGN PATENT DOCUMENTS

WO WO-2020093084 A1 * 5/2020 .......... A61M 60/508

OTHER PUBLICATIONS

International Search Report and Written Opinion for International Application No. PCT/US2023/082867 mailed Feb. 26, 2024, 18 pages.

*Primary Examiner* — Manolis Pahakis
(74) *Attorney, Agent, or Firm* — Pierce Atwood LLP

(57) ABSTRACT

Methods and apparatus for determining a contractile reserve of a heart of a patient are provided. The method includes controlling a heart pump to operate at a first speed, determining based on a motor current signal received from a motor when the heart pump is operating at the first speed, a first value for a cardiac contractility metric, controlling the heart pump to operate at a second speed, determining based, at least in part, on the motor current signal received from the motor when the heart pump is operating at the second speed, a second value for the cardiac contractility metric, determining a contractile reserve metric based, at least in part, on the first value and the second value of the cardiac contractility metric, and outputting an indication of the contractile reserve metric on a user interface associated with the heart pump.

20 Claims, 7 Drawing Sheets

(51) Int. Cl.

| | |
|---|---|
| ***A61M 60/17*** | (2021.01) |
| ***A61M 60/216*** | (2021.01) |
| ***A61M 60/531*** | (2021.01) |
| ***A61M 60/585*** | (2021.01) |
| ***G16H 40/63*** | (2018.01) |

(52) U.S. Cl.

CPC ........ *A61M 60/216* (2021.01); *A61M 60/531* (2021.01); *A61M 60/585* (2021.01); *G16H 40/63* (2018.01); *A61M 2230/30* (2013.01)

(56) References Cited

U.S. PATENT DOCUMENTS

| | | | | |
|---|---|---|---|---|
| 2018/0078159 | A1* | 3/2018 | Edelman | A61B 5/02141 |
| 2018/0353667 | A1* | 12/2018 | Moyer | A61B 5/0215 |
| 2020/0060559 | A1* | 2/2020 | Edelman | A61B 5/02141 |
| 2020/0147284 | A1* | 5/2020 | Meki | A61M 60/538 |
| 2022/0152376 | A1* | 5/2022 | Kudlik | A61M 60/422 |
| 2022/0167862 | A1* | 6/2022 | Edelman | A61B 5/02141 |
| 2024/0347189 | A1* | 10/2024 | Zhang | A61B 5/02028 |

* cited by examiner

ESTIMATING CONTRACTILE RESERVE USING A MECHANICAL CIRCULATORY SUPPORT DEVICE

CROSS-REFERENCE TO RELATED APPLICATIONS

This application claims the benefit under 35 U.S.C. § 119(e) to U.S. Provisional Patent Application No. 63/431,208, filed Dec. 8, 2022, and titled, "ESTIMATING CONTRACTILE RESERVE USING A MECHANICAL CIRCULATORY SUPPORT DEVICE," the entire contents of which is incorporated by reference herein.

FIELD OF THE INVENTION

This disclosure relates to techniques for estimating contractile reserve using a mechanical circulatory support device.

BACKGROUND

Cardiovascular diseases are a leading cause of morbidity, mortality, and burden on global healthcare. A variety of treatment modalities have been developed for heart health, ranging from pharmaceuticals to mechanical devices and transplantation. Temporary cardiac support devices, such as heart pump systems, provide hemodynamic support and facilitate heart recovery. Some heart pump systems may be percutaneously inserted into the heart and can operate in parallel with the native heart to supplement cardiac output. Examples of such devices include the Impella® family of devices (Abiomed, Inc., Danvers, MA). Such heart pump systems may have sensors that detect blood pressure (or assess differential pressures across membranes) and may monitor motor current, and may use the sensor and motor current readings to help identify pump positioning.

Such pumps can be positioned, for example, in a cardiac chamber, such as the left ventricle, to assist the heart. In this case, the pump may be inserted via a femoral artery by means of a hollow catheter and introduced up to and into the left ventricle of a patient's heart. From this position, the pump inlet may draw in blood and the pump outlet may expel the blood into the aorta. In this manner, the heart's function may be replaced or at least assisted by operation of the pump.

An intravascular pump is typically connected to a respective external heart pump controller that controls the pump, such as its motor speed, and collects and displays operational data about the blood pump, such as heart signal level, battery temperature, blood flow rate and plumbing integrity. An exemplary heart pump controller is available from Abiomed, Inc. under the trade name Automated Impella Controller®. The controller raises alarms when operational data values fall beyond predetermined values or ranges, for example if a leak, suction, and/or pump malfunction is detected. The controller may include a video display screen upon which is displayed a graphical user interface configured to display the operational data and/or alarms.

SUMMARY

Described herein are systems and methods for determining a contractile reserve metric for a heart of patient having a mechanical circulatory support device arranged therein In some embodiments, a method of determining a contractile reserve of a heart of a patient having a mechanical circulatory support device arranged therein. The method includes controlling the mechanical circulatory support device to operate at a first performance level, determining based, at least in part, on a motor current signal received from a motor when the mechanical circulatory support device is operating at the first performance level, at least one first value for a cardiac contractility metric, controlling the mechanical circulatory support device to operate at a second performance level, determining based, at least in part, on the motor current signal received from the motor when the mechanical circulatory support device is operating at the second performance level, at least one second value for the cardiac contractility metric, determining a contractile reserve metric based, at least in part, on the at least one first value and the at least one second value of the cardiac contractility metric, and outputting an indication of the contractile reserve metric on a user interface associated with the mechanical circulatory support device.

In one aspect, the mechanical circulatory support device is configured to operate at a predetermined number of performance levels including the first performance level and the second performance level. The method further comprises controlling the mechanical circulatory support device to operate at each of the predetermined number of performance levels, and determining based, at least in part, on the motor current signal received from the motor when the mechanical circulatory support device is operating at each of the predetermined number of performance levels, a corresponding at least one value for the cardiac contractility metric. The contractile reserve metric is determined based, at least in part, on the at least one value determined when the mechanical circulatory support device was operating at each of the predetermined number of performance levels.

In one aspect, the method further comprises receiving, from a pressure sensor associated with the mechanical circulatory support device, a pressure signal, the at least one first value for the cardiac contractility metric is determined based, at least in part, on the pressure signal when the mechanical circulatory support device was operating at the first performance level, and the at least one second value for the cardiac contractility metric is determined based, at least in part, on the pressure signal when the mechanical circulatory support device was operating at the second performance level.

In one aspect, the at least one first value for the cardiac contractility metric and/or the at least one second value for the cardiac contractility metric is determined based, at least in part, on data stored in data storage associated with the mechanical circulatory support device.

In one aspect, determining a contractile reserve metric based, at least in part, on the at least one first value for the cardiac contractility metric and the at least one second value for the cardiac contractility metric comprises analyzing a variance between the at least one first value for the cardiac contractility metric and the at least one second value for the cardiac contractility metric.

In one aspect, the cardiac contractility metric includes a contractility index. In one aspect, the cardiac contractility metric includes a contractility score. In one aspect, outputting an indication of the contractile reserve metric comprises displaying on the user interface, a graph of the at least one value for the cardiac contractility metric determined at each of the first and second performance levels. In one aspect, outputting an indication of the contractile reserve metric comprises displaying on the user interface, a numerical value for the contractile reserve metric.

In some embodiments, a mechanical circulatory support device is provided. The mechanical circulatory support device includes a rotor, a motor configured to drive rotation of the rotor at a plurality of speeds, and at least one controller. The at least one controller is configured to control the motor to operate at a first speed, determine based, at least in part, on a motor current signal received from the motor when operating at the first speed, at least one first value for a cardiac contractility metric, control the motor to operate at a second speed, determine based, at least in part, on a motor current signal received from the motor when operating at the second speed, at least one second value for the cardiac contractility metric, determine a contractile reserve metric based, at least in part, on the at least one first value for the cardiac contractility metric and the at least one second value for the cardiac contractility metric, and output an indication of the contractile reserve metric on a user interface associated with the mechanical circulatory support device.

In one aspect, the at least one controller is further configured to control the motor to operate at a predetermined number of speeds including the first speed and the second speed, and determine based, at least in part, on the motor current signal received from the motor when the motor is operating at each of the predetermined number of speeds, a corresponding at least one value for the cardiac contractility metric. The contractile reserve metric is determined based, at least in part, on the at least one value determined when the motor was operating at each of the predetermined number of speeds.

In one aspect, the mechanical circulatory support device further includes a pressure sensor configured to measure a pressure signal, the at least one first value for the cardiac contractility metric is determined based, at least in part, on the pressure signal when the motor was operating at the first speed, and the at least one second value for the cardiac contractility metric is determined based, at least in part, on the pressure signal when the motor was operating at the second speed.

In one aspect, the mechanical circulatory support device further includes data storage, and the at least one first value for the cardiac contractility metric and/or the at least one second value for the cardiac contractility metric is determined based, at least in part, on data stored the data storage.

In one aspect, determining a contractile reserve metric based, at least in part, on the at least one first value for the cardiac contractility metric and the at least one second value for the cardiac contractility metric comprises analyzing a variance between the at least one first value for the cardiac contractility metric and the at least one second value for the cardiac contractility metric.

In one aspect, the cardiac contractility metric includes a contractility index. In one aspect, the cardiac contractility metric includes a contractility score. In one aspect, outputting an indication of the contractile reserve metric comprises displaying on the user interface, a graph of the at least one value for the cardiac contractility metric determined at each of the first and second speeds. In one aspect, outputting an indication of the contractile reserve metric comprises displaying on the user interface, a numerical value for the contractile reserve metric.

In some embodiments, a controller for a mechanical circulatory support device is provided. The controller includes at least one hardware processor configured to control a motor of the mechanical circulatory support device to operate at a first speed, determine based, at least in part, on a motor current signal received from the motor when operating at the first speed, at least one value for a cardiac contractility metric, control the motor to operate at a second speed, determine based, at least in part, on a motor current signal received from the motor when operating at the second speed, at least one second value for the cardiac contractility metric, determine a contractile reserve metric based, at least in part, on the at least one first value for the cardiac contractility metric and the at least one second value for the cardiac contractility metric, and output an indication of the contractile reserve metric on a user interface associated with the mechanical circulatory support device.

In one aspect, the at least one hardware processor is further configured to control the motor to operate at a predetermined number of speeds including the first speed and the second speed, and determine based, at least in part, on the motor current signal received from the motor when the motor is operating at each of the predetermined number of speeds, a corresponding at least one value for the cardiac contractility metric. The contractile reserve metric is determined based, at least in part, on the at least one value determined when the motor was operating at each of the predetermined number of speeds.

In one aspect, the at least one hardware processor is further configured to receive, from a pressure sensor associated with the mechanical circulatory support device, a pressure signal, the at least one first value for the cardiac contractility metric is determined based, at least in part, on the pressure signal when the motor was operating at the first speed, and the at least one second value for the cardiac contractility metric is determined based, at least in part, on the pressure signal when the motor was operating at the second speed.

In one aspect, the controller further includes data storage, and the at least one first value for the cardiac contractility metric and/or the at least one second value for the cardiac contractility metric is determined based, at least in part, on data stored in the data storage.

In one aspect, determining a contractile reserve metric based, at least in part, on the at least one first value for the cardiac contractility metric and the at least one second value for the cardiac contractility metric comprises analyzing a variance between the at least one first value for the cardiac contractility metric and the at least one second value for the cardiac contractility metric.

In one aspect, the cardiac contractility metric includes a contractility index. In one aspect, the cardiac contractility metric includes a contractility score. In one aspect, outputting an indication of the contractile reserve metric comprises displaying on the user interface, a graph of the at least one value for the cardiac contractility metric determined at each of the first and second speeds. In one aspect, outputting an indication of the contractile reserve metric comprises displaying on the user interface, a numerical value for the contractile reserve metric.

In some embodiments, a method of determining cardiac functional capacity for a patient having an implanted mechanical circulatory support device is provided. The method comprises dynamically modulating a level of support provided by the mechanical circulatory support device to the patient, and assessing a cardiac response to the dynamically modulating levels of support to determine a cardiac functional capacity for the patient.

In some embodiments, a method of optimizing control of a mechanical circulatory support device for a patient is provided. The method comprises assessing at a first time, a first cardiac response of the patient to dynamic modulation of levels of support provided by the mechanical circulatory support device to the patient, assessing at a second time, a second cardiac response of the patient to dynamic modulation of levels of support provided by the mechanical circulatory support device to the patient, and controlling an operation of the mechanical circulatory support device at a third time based on the first cardiac response and the second cardiac response.

DETAILED DESCRIPTION

The systems, devices, and methods described herein enable a support device (e.g., a mechanical circulatory support device) residing completely or partially within an organ to assess one or more aspects of that organ's function. In particular, the systems, devices, and methods described herein enable heart pump systems, such as percutaneous ventricular assist devices, to be used to assess the function of the heart. For example, such devices may be used to estimate contractile reserve of a patient's myocardium.

Assessing the function of the heart using a heart pump system can alert health professionals to changes in cardiac function and allow the professional to tailor the degree/level of support provided by the support device (e.g., flow rate of blood pumped by the device) based on a particular patient's needs. For example, the degree of support can be increased when a patient's heart function is deteriorating, or the degree of support can be decreased when a patient's heart function is recovering and returning to a baseline of normal heart function. This can allow the device to dynamically respond to changes in heart function to promote heart recovery and can allow the patient to be gradually weaned off of that therapy. Furthermore, assessment of the heart function can indicate when it is appropriate to terminate use of the heart pump system. Although some embodiments presented herein are directed to heart pump systems implanted across the aortic valve and residing partially in the left ventricle, the concepts described herein can be applied to devices in other regions of the heart, the cardiovascular system, or the body.

Continuous measurement of vascular and cardiac performance by using the effects of a heart pump system can provide additional clinical data to aid in titration of appropriate device support. The mechanical circulatory support systems presented herein reside within the heart and may work in parallel with native ventricular function. This may allow the systems to be sensitive enough to detect native ventricular function unlike some more invasive devices. Thus, the systems, devices, and methods described herein enable the use of mechanical circulatory support systems not only as support devices, but also as diagnostic and prognostic tools. The heart pump systems can function as sensors that extract information about cardiac function by hydraulically coupling with the heart. In some implementations, the heart pump systems described herein may be configured to operate at a constant performance level (e.g., constant rotational speed of a rotor), while power delivered to the assist device is measured. In certain implementations, the speed of the rotor of the heart pump system may be varied (e.g., as a delta, step, or ramp function) to further probe the native heart function.

Figure 1:
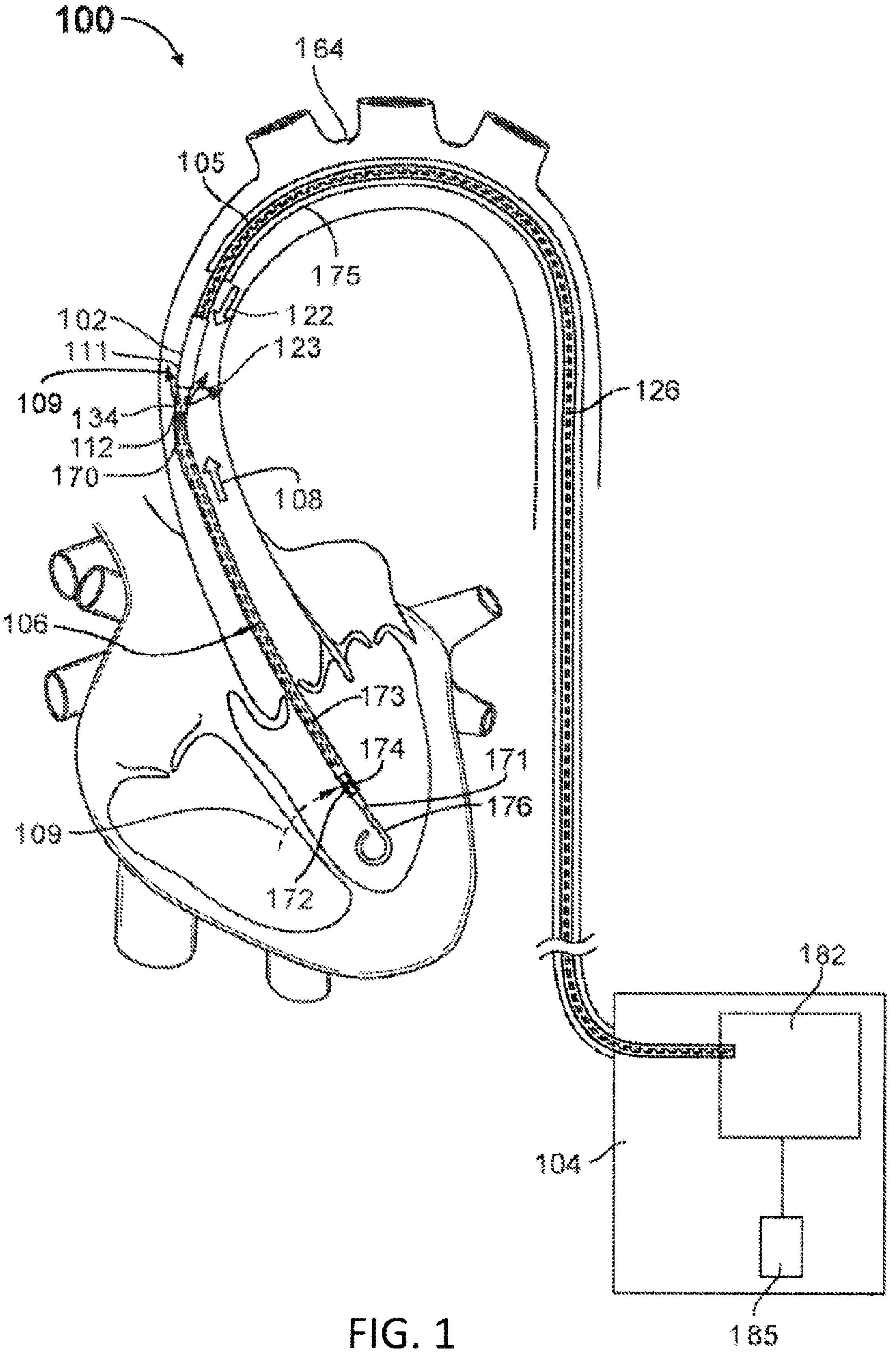
FIG. 1 illustrates a heart pump system inserted into a blood vessel of a patient in accordance with some embodiments of the present technology.

FIG. 1 shows an illustrative heart pump system inserted into a blood vessel of a patient. As an example, heart pump systems compatible with the present disclosure are disclosed in U.S. Pat. No. 11,357,968, the contents of which are hereby incorporated by reference in their entirety. Generally, any other heart pump system or other mechanical circulatory support system (and sensor for obtaining physiological data from a patient) may be used with the techniques described herein. In some implementations, the systems and methods described herein may use expandable pumps (e.g., Heartmate PHP™ family of devices (Thoratec Corporation)) or left atrium-to-femoral artery bypass pumps (e.g., TandemHeart family of devices (Livallova, PLC)). In some implementations, the systems and methods described herein may use the Impella® family of devices (Abiomed, Inc., Danvers, MA).

The heart pump system 100 may operate within a heart, partially within the heart, outside the heart, partially outside the heart, partially outside the vascular system, or in any other suitable location in a patient's vascular system. The heart pump system may be considered "in position" when cannula 173 is placed across the aortic valve such that a blood inlet (e.g., blood inlet 172) to the pump is within the left ventricle and an outlet (e.g., outlet openings 170) from the pump is within the aorta. The heart pump system 100 may include a heart pump 106 and a control system 104. All or part of the control system 104 may be in a controller unit separate/remote from the heart pump 106. In some implementations, at least a portion of the control system 104 is internal to the heart pump 106. The heart pump system 100 may include an elongate catheter 105, a motor housing 102 and a drive shaft in which a pump element is formed. The heart pump system 100 also may include a pump housing 134, and a motor housing 102 coupled to cannula 173 at a distal end 111 of the motor housing 102. An impeller blade on the drive shaft may be rotated within a pump housing 134 to induce a flow of blood into the cannula 173 at a suction head 174. The suction head 174 provides a blood inlet 172 at the distal end portion 171 of the cannula 173. The flow 109 of blood may pass through the cannula 173 in a first direction 108 and exits the cannula 173 at one or more outlet openings 170 of the cannula 173.

The rotation of the drive shaft within the pump housing 134 may rotate a pump element within a bearing gap. A hemocompatible fluid may be delivered through the elongate catheter 105 through the motor housing 102 to a proximal end portion of the cannula 173 where the fluid lubricates the pump. The flow of hemocompatible fluid may have a second direction 122 through the bearing gap of the pump. After exiting the bearing gap, the hemocompatible fluid may follow flow direction 123 and becomes entrained in the flow of blood and flows into the aorta with the blood.

The heart pump 106 may be inserted into a vessel of the patient through a sheath 175. The pump housing 134 encloses the rotor and internal bearings and may be sized for percutaneous insertion into a vessel of a patient. In some implementations, the pump is advanced through the vasculature and over the aortic arch 164. Although the pump is shown in the left ventricle, the pump may alternatively be placed in the right side of the heart, such that the blood is pumped from the patient's inferior vena cava or right atrium, through the right ventricle into the pulmonary artery.

A flexible projection 176 may be included at a distal end portion 171 of the cannula 173, distal to the suction head 174, in order to stabilize the heart pump 106 in a vessel or chamber of the heart. The flexible projection 176 may be atraumatic and helps prevent the suction head 174 from approaching the wall of the vessel where it may become stuck due to suction. The flexible projection 176 extends the heart pump 106 mechanically, but not hydraulically, as the flexible projection 176 is non-sucking. In some implementations, the flexible projection may be formed as a pigtail. In some aspects, the pump need not include a flexible projection.

The elongate catheter 105 houses a connection 126 with a fluid supply line and electrical connection cables. The connection 126 also supplies a hemocompatible fluid to the pump from a fluid reservoir and is contained within control system 104.

The control system 104 includes controller 182 that s heart pump 106 by delivering power to the motor and controlling the motor speed. The control system 104 includes circuitry for monitoring the motor current for drops in current indicating air in the line, changes in differential pressure signal, flow position, suction, or any other suitable measurement. In some implementations, the control system 104 includes display screens to show measurements such as a differential pressure signal and motor current. The control system 104 may include warning sounds, lights or indicators to alert an operator of sensor failures, disconnects or breaks in the connection 126, or sudden changes to patient health.

The heart pump may operate at a variety of pump speeds or P-levels. P-level is the performance level of the heart pump system and related to flow control of the system. As the P-level increases, the flow rate, motor current, and revolutions per minute associated with the heart pump system increase; thus, higher P-levels correspond to higher flow rates and revolutions per minute associated with the heart pump system. For example, power level P-1 may correspond to a first number of rotations per minute (RPM) for the rotor, while power level P-2 may correspond to a second number of RPM. In some examples, the pump operates at ten different power levels ranging from P-0 through P-9. These P-levels may correspond to 0 RPM through 100,000 RPM or any suitable number. Changing the speed of the rotor changes the cardiac output of the heart.

The control system 104 includes a current sensor (not shown). The controller 182 supplies current to the motor by the connection 126 such as through one or more electrical wires. The current supplied to the motor via the connection 126 is measured by the current sensor. The load that the motor of a mechanical pump experiences corresponds to the force of the pressure head, or the difference between the aortic and left ventricular pressure. The heart pump 106 experiences a nominal load during steady state operation for a given pressure head, and variations from this nominal load are a result of changing external load conditions, for example the dynamics of left ventricular contraction. Changes to the dynamic load conditions alter the motor current required to operate the pump rotor at a constant, or substantially constant, speed. The motor may operate at a speed required to maintain the rotor at a set speed, and the motor current drawn by the motor to maintain the rotor speed can be monitored and used to detect the underlying cardiac state. The cardiac state can be even more precisely quantified and understood by simultaneously monitoring the pressure head during the cardiac cycle using a pressure sensor 112 with regard to the motor current to generate a hysteresis loop of quantitative pump performance that may be analyzed to determine changes in the cardiac state and function.

Various implementations of pressure sensors may be used. One example is an optical sensor, or a differential sensor. The differential pressure sensor is a flexible membrane integrated into the cannula 173. One side of the sensor is exposed to the blood pressure on the outside of the cannula and the other side is exposed to the pressure of the blood inside of the cannula. The sensor generates an electrical signal (the differential pressure signal) proportional to the difference between the pressure outside the cannula and the pressure inside, which may be displayed by the heart pump system. When the heart pump system is placed in the correct position across the aortic valve, the top (outer surface) of the sensor is exposed to the aortic pressure and the bottom (inner surface) of the sensor is exposed to the ventricular pressure. Therefore, the differential pressure signal is approximately equal to the difference between the aortic pressure and the ventricular pressure. Other sensors, such as an optical sensor or a fluid filled column, may be used.

The heart parameter estimator 185 is configured to receive motor current signals from the current sensor and pressure signals from the pressure sensor 112. The heart parameter estimator 185 may use one or both of the motor current and pressure signals to characterize aspects of the heart's function. For instance, the heart parameter estimator 185 may determine one or more cardiac function parameters using a model of the combined heart and heart pump system. In one method of cardiac function determination, the model includes stored data, which may be implemented as a look-up table or a predetermined/normalized pump performance curve or calibration curve or any other suitable model. A look-up table may include data describing the power required to maintain a rotational speed and pressure head determined as a function of pump flow, and a set of curves relating the pressure head and the flow characteristics of the heart may be determined. For example, a look-up table may indicate that a particular aortic pressure and motor current corresponds to a particular left ventricular end diastolic pressure (LVEDP). In another method of cardiac function determination, the performance of the pump is represented by showing the pressure head as a function of the motor current draw of the pump, the current draw acting as a surrogate for the power or load on the pump. The relationship between the motor current draw and the pressure head during the cardiac cycle describes a hysteresis curve or loop. Cardiac state and functions, including left ventricular pressure (LVP) and LVEDP can be extracted from the relationship between the motor current draw and pressure head. Instead of or in addition to LVEDP, cardiac function can be quantified in other ways using the mechanical support devices presented herein. For example, heart function can be expressed as contractility, stroke volume, ejection fraction, chamber pressure, stroke work, cardiac output, cardiac power output, LVEDP, preload state, afterload state, heart rate, and/or heart recovery.

To accurately determine at least some of these cardiac function parameters, hysteresis between the pressure measurements (e.g., difference between aortic pressure and left ventricular pressure, or the aortic pressure alone) and the motor current measurements may be taken into account, as described herein. This hysteresis can be accounted for by detecting the phase of the cardiac cycle corresponding to a given pair of pressure and current measurements. This can be done using at least two methods that differentiate diastolic filling from the other phases of the cardiac cycle. Both methods identify critical points which indicate the beginning and end of diastolic filling. The first method uses the aortic pressure waveform and identifies key characteristics in the curve, such as the dicrotic notch, to indicate the beginning of diastolic filling. This method can also use the beginning of aortic filling to indicate the end of diastolic ventricular filling. The second method uses ECG data timed with the pressure tracings to identify two characteristics that demarcate diastolic filling, such as the beginning of the QRS complex and the end of the T-wave. If there is noise in the signal, it can be more reliable to detect the peak of the QRS complex (the R-wave) and the peak of the T-wave. Furthermore, in some implementations, the hysteresis between the pressure and motor parameter measurements can itself be used to determine the phase of the cardiac cycle. Heart parameter estimator 185 may be implemented as software programmed in controller 182, or may be implemented, at least in part, as separate hardware connected to controller 182 by a wired or wireless connection. Heart parameter estimator 185 may be configured to execute one or more of the algorithms described herein. For example, heart parameter estimator 185 may be configured to estimate cardiac contractility metrics based, at least in part, on the motor current delivered to the pump.

Various heart parameters indicative of cardiac function can also be determined by the heart parameter estimator 185 based on a comparison of measured values to look-up tables or from the shape and values of hysteresis loops formed from the measured motor parameters and pressure during the cardiac cycle. For example, changes in contractility can be related to the variation in slope of the pressure during contraction of the heart (dP/dt). The cardiac output may be determined based on the flow rate of the blood through and past the pump. The stroke volume is an index of left ventricular function with a formula SV=CO/HR, where SV is the stroke volume, CO is the cardiac output, and HR is the heart rate. Stroke work is the work done by the ventricle to eject a volume of blood and can be calculated from the stroke volume according to the equation SW=SV*MAP, where SW is the stroke work, SV is the stroke volume, and MAP is the mean arterial pressure. Cardiac work is calculated by the product of stroke work and heart rate. Cardiac power output is a measure of the heart function in Watts calculated using the equation CPO=mAoP*CO/451, where CPO is the cardiac power output, mAoP is the mean aortic pressure, CO is the cardiac output, and 451 is a constant used to convert mmHG×L/min into Watts. The ejection fraction can be calculated by dividing the stroke volume by the volume of blood in the ventricle. Other parameters, such as chamber pressure, preload state, afterload state, heart recovery, flow load state, variable volume load state, and/or cardiac cycle flow state can be calculated from these values or determined by examination of the hysteresis loop.

In some embodiments, the heart parameter estimator 185 may be configured to determine a metric of cardiac contractility based, at least in part, on the motor current and/or the pressure. In some implementations, the metric of cardiac contractility may be a coefficient of contractility that represents the inherent strength and vigor of the heart's contraction during systole. The stroke volume of the heart will be greater if the contractility of the heart is greater. For example, medium contractility may occur when the stroke volume of the heart is about 65 mL. High contractility may occur when the stroke volume of the heart is over 100 mL. Low contractility may occur when the stroke volume of the heart is less than 30 mL. The contractility score may be expressed numerically and/or graphically. The contractility score may be non-dimensional.

Figure 2:
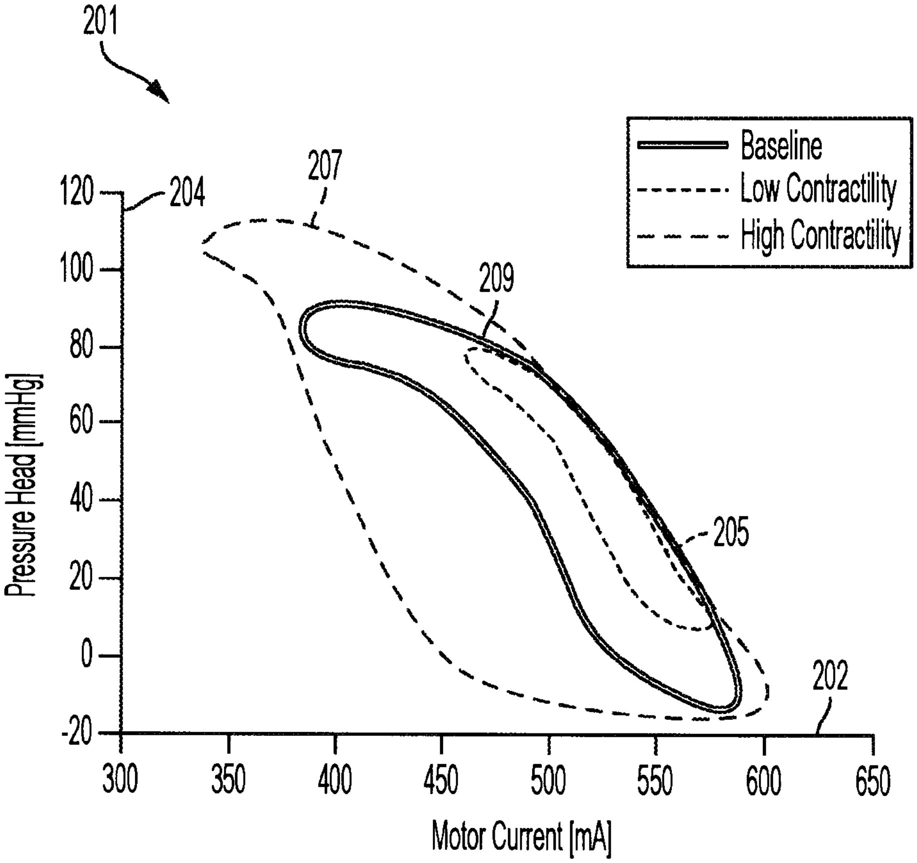
FIG. 2 illustrates a smoothed curve of a plot of pressure head as a function of motor current.

FIG. 2 depicts a plot 201 having an x-axis 202 showing current in units of mA and a y-axis 204 showing pressure head between the left ventricle and the aorta in units of mmHg. The plot 201 shows three curves, a baseline curve 209, a curve showing low contractility 205, and a curve showing high contractility 207. The smooth curves of FIG. 2 allow a healthcare professional to visualize the changes in the behavior of the heart, for example after the administration of beta-blockers, as in the low contractility state, and can be used to extract meaningful cardiac parameters and changes in heart health. While FIG. 2 includes the hysteresis curves shown on x-axis 202 of motor current in units of mA, the hysteresis curves may be plotted with any motor parameter which varies with time and pulse on the x-axis.

Figure 3A:
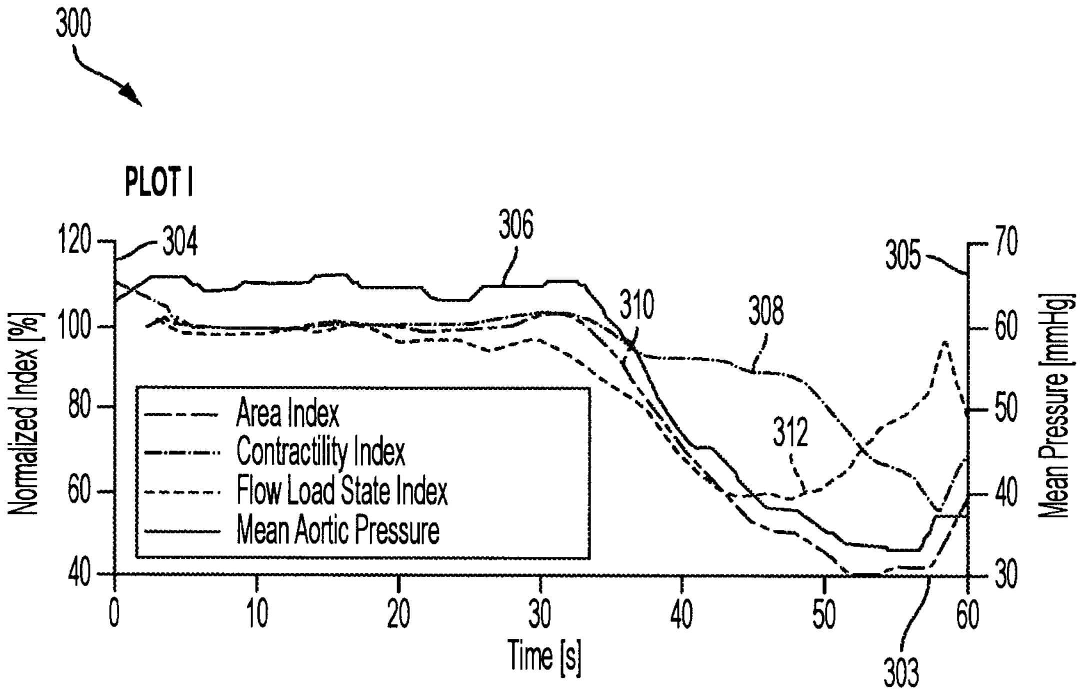
FIGS. 3A to 3C illustrate a series of plots of mock loop data with varied contractility under a constant load.
Figure 3B:
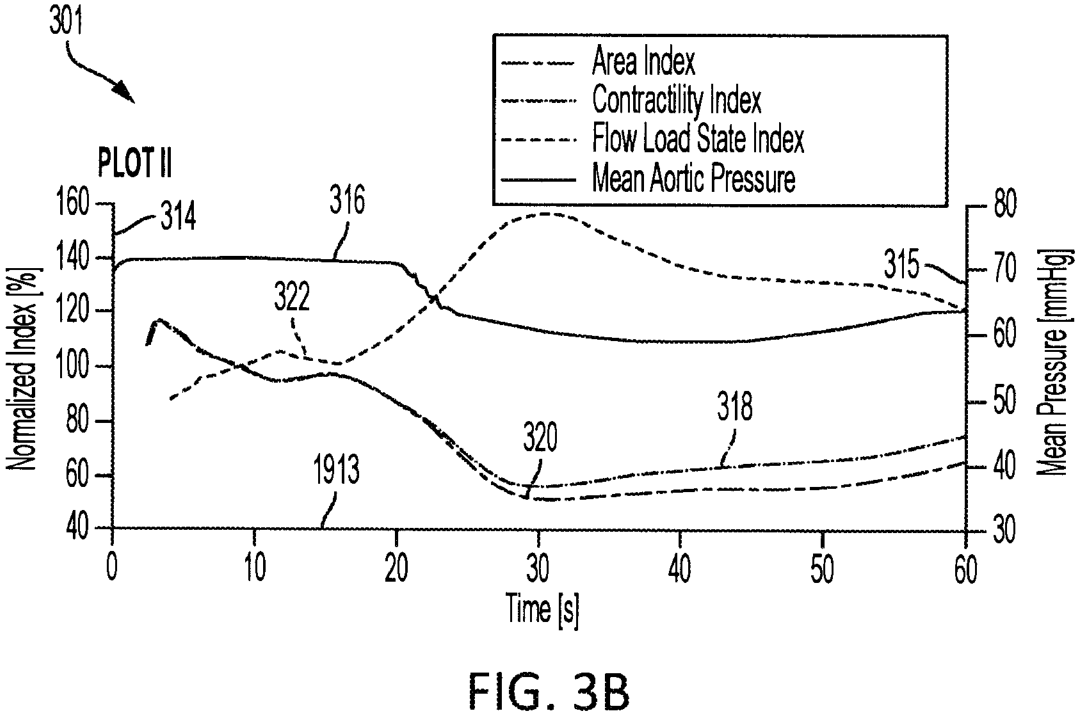
Figure 3C:
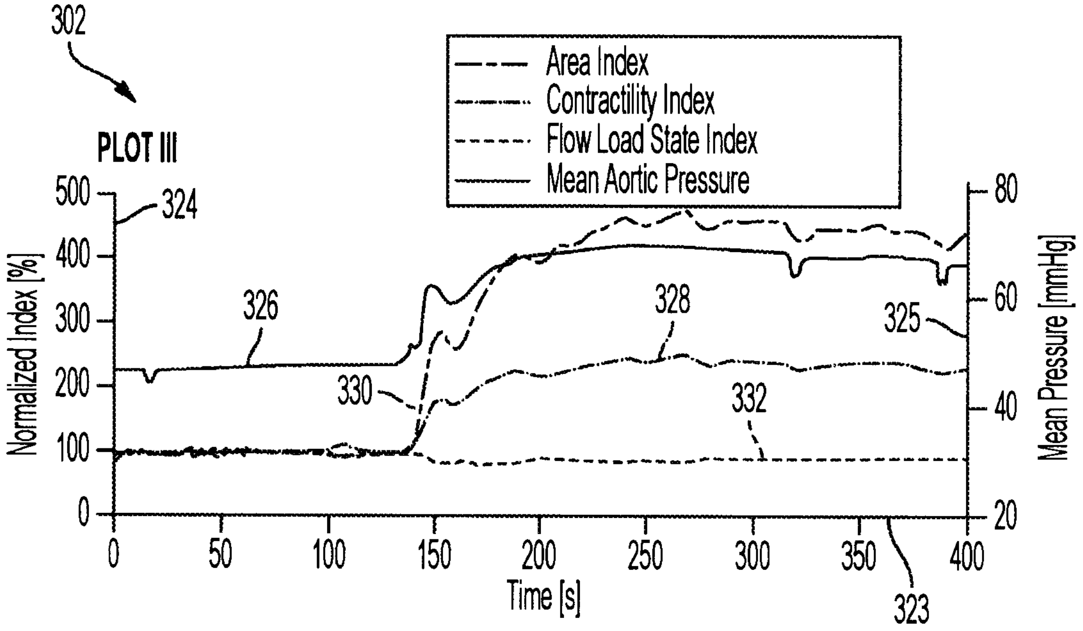

FIGS. 3A to 3C show examples of various cardiac parameters over time illustrating the diagnostic capabilities afforded by visualizing the parameters. Each of the plots shows data generated from an animal model showing changes in the area index, contractility, flow load state, and mean aortic pressure over time. Plot I 300 shown in FIG. 3A includes an x-axis 303 representing time in seconds, a first y-axis 304 representing the normalized index as a percent and a second y-axis 305 representing mean pressure in mmHg. Plot I includes tracings of the area index 310 (indicative of overall heart function), contractility index 308, flow load state index 312, and mean aortic pressure 306 during a balloon occlusion of the inferior vena cava.

Plot II 301 shown in FIG. 3B includes an x-axis 313 representing time in seconds, a first y-axis 314 representing the normalized index as a percent, and a second y-axis 315 representing mean pressure in mmHg. Plot II includes tracings of the arca index 320, contractility index 318, flow load state 322, and mean aortic pressure 316 following the use of a beta blocker.

Plot III 302 shown in FIG. 3C includes an x-axis 323 representing time in seconds, a first y-axis 324 representing the normalized index as a percent, and a second y-axis 325 representing mean pressure in mmHg. Plot III includes tracings of the area index 330, contractility index 328, flow load state 332, and mean aortic pressure 326 following use of an inotrope.

The plots I-III of FIGS. 3A-3C illustrate the different responses in the various measurable cardiac parameters in response to various cardiac events. For example, the decrease in heart function illustrated by the decrease in the area index 310 in plot I is preceded by a decrease in the flow load state index 312, indicating that there is a problem with the volume of blood pumped by the heart. The decrease in the area index 320 in plot II coincides with the decrease of the contractility index 318, indicating that the beta blocker administered to the animal model has affected contractility of the heart. The cardiac parameters displayed in plots I-III can be calculated from hysteresis loops and displayed to illustrate changes in the contractility state, flow load state, and overall cardiac function, and to determine the cause of such changes.

Understanding the trends in various cardiac parameters for a patient allows a trained medical professional to better address a patient's cardiac needs. The state of a patient's heart can be determined by a health care professional through the changes and trends in the various calculated cardiac parameters.

Figure 4A:
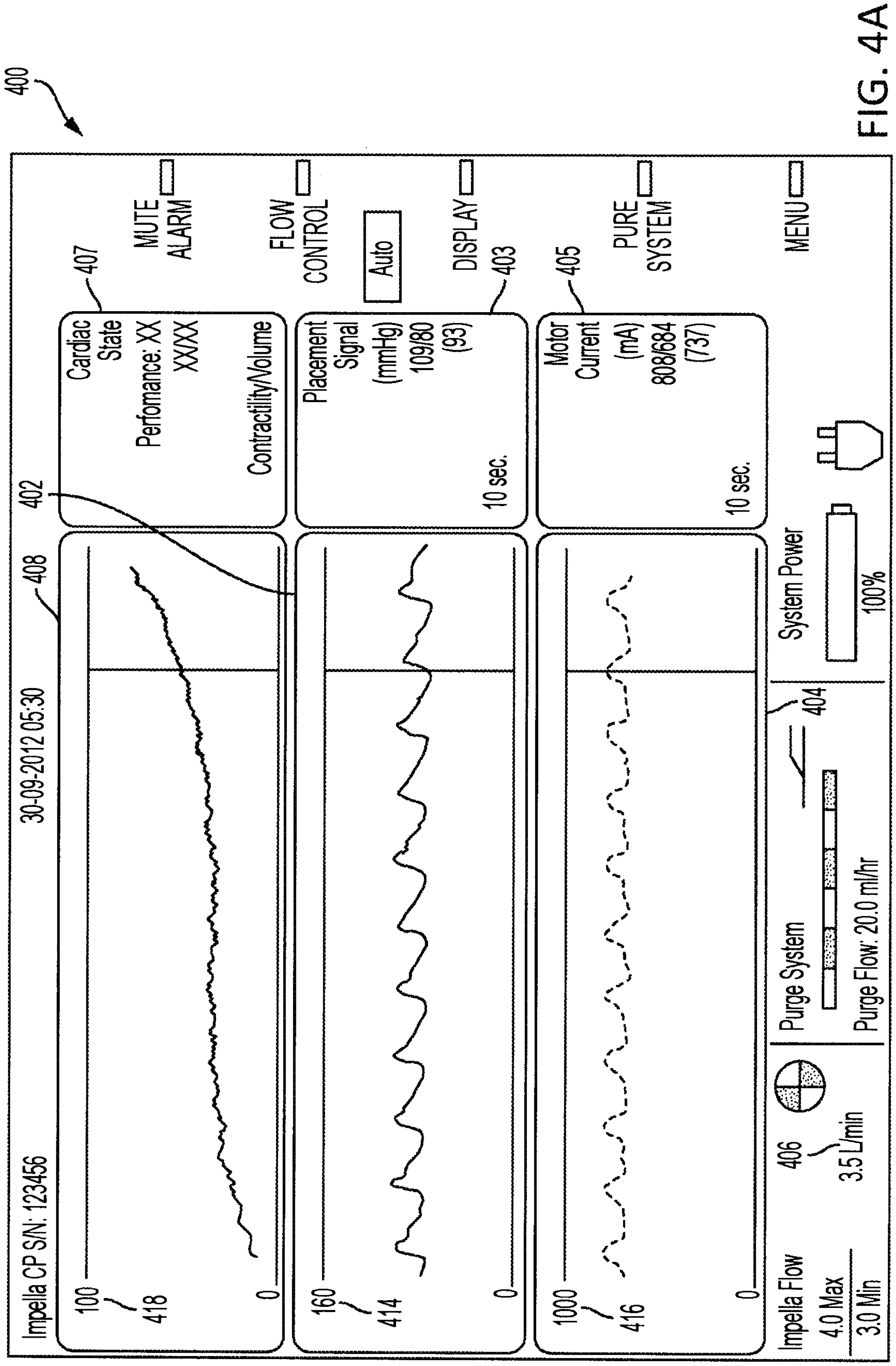
FIG. 4A illustrates an exemplary user interface for a heart pump controller displaying measurements over time.

FIG. 4A shows an example user interface 400 for a heart pump controller that includes a waveform of a metric of cardiac function over time. The user interface 400 may be used to control operation of the intravascular heart pump system 100 of FIG. 1 or any other suitable heart pump system. The user interface 400 includes a pressure signal waveform 402, a motor current waveform 404, a cardiac state waveform 408, and a flow rate 406. The pressure signal waveform 402 indicates the pressure measured by the blood pump's pressure sensor (e.g., pressure sensor 112). The pressure signal waveform 402 can be used by a healthcare professional to properly place an intravascular heart pump (such as intravascular heart pump 106 in FIG. 1) in the heart. The pressure signal waveform 402 may be used to verify the position of the intravascular heart pump by evaluating whether the waveform 402 is an aortic or ventricular waveform. An aortic waveform indicates that the intravascular heart pump motor is in the aorta. A ventricular waveform indicates that the intravascular heart pump motor has been inserted into the ventricle which is the incorrect location. A scale 414 for the placement signal waveform is displayed to the left of the waveform. The default scaling is 0-160 mmHg. It can be adjusted in 20 mmHg increments. To the right of the waveform is a display 403 that labels the waveform, provides the units of measurement, and shows the maximum and minimum values and the average value from the samples received.

The motor current waveform 404 is a measure of the energy intake of the heart pump's motor. The energy intake varies with the motor speed and the pressure difference between the inlet and outlet areas of the cannula resulting in a variable volume load on the rotor. When used with an intravascular heart pump (such as intravascular heart pump 106 in FIG. 1), the motor current provides information about the catheter position relative to the aortic valve. When the intravascular heart pump is positioned correctly, with the inlet area in the ventricle and the outlet area in the aorta, the motor current is pulsatile because the mass flow rate through the heart pump changes with the cardiac cycle. When the inlet and outlet areas are on the same side of the aortic valve, the motor current will be dampened or flat because the inlet and outlet of the pump are located in the same chamber and there is no variability in differential pressure resulting in a constant mass flow rate, and subsequently constant motor current. A scale 416 for the motor current waveform is displayed to the left of the waveform. The default scaling is 0-1000 mA. The scaling may be adjustable in 100 mA increments. To the right of the waveform is a display 405 that labels the waveform, provides the units of measurement, and shows the maximum and minimum values and the average value from the samples received.

The cardiac state waveform 408 is a display of the recorded cardiac state over a period of time. The cardiac state may be displayed as a ratio of the contractility of the heart divided by the volume of blood pumped. The cardiac state may be calculated at discrete time points or continuously and displayed in the cardiac state waveform 408 as a trend in order to provide a physician with an indicator of the current performance of the heart relative to the performance at other points in time in the patient's treatment. A scale 418 for the cardiac state waveform 408 is displayed to the left of the cardiac state trend line. The default scaling is from 1-100 (unitless). The scaling may be adjusted to best show the cardiac state trend. To the right of the cardiac state waveform 408 is a display 407 that labels the trend line, provides additional information about the cardiac performance at the current time, and shows the current values of contractility and volume received from the pump. The display of this information as a trend line allows a physician to view the historical cardiac state of a patient and to make decisions based on the trend of the cardiac state. For example, a physician may observe from the cardiac state trend line a decline or an increase in the cardiac state over time and determine to alter or continue treatment based on this observation.

The flow rate 406 can be a target blood flow rate set by the user or an estimated actual flow rate. In some modes of the controller, the controller will automatically adjust the motor speed in response to changes in afterload to maintain a target flow rate. In some implementations, if flow calculation is not possible, the controller will allow a user to set a fixed motor speed as indicated by speed indicator 428.

Figure 4B:
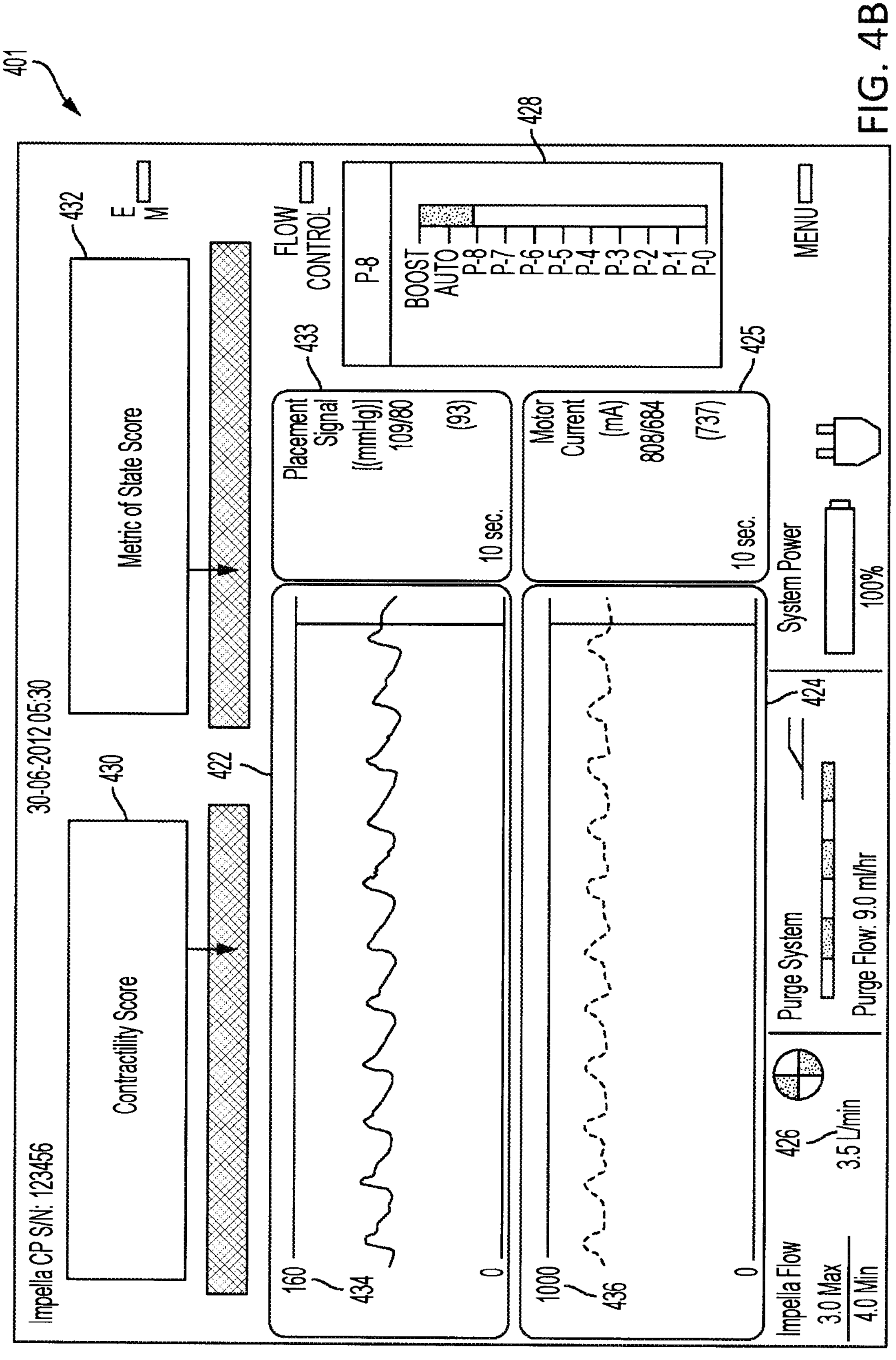
FIG. 4B illustrates an exemplary user interface for a heart pump controller.

FIG. 4B shows an example user interface 401 for a heart pump controller according to certain implementations. The user interface 401 may be used to control operation of the intravascular heart pump system 100 of FIG. 1, or any other suitable heart pump system. The user interface 401 includes a pressure signal waveform 422, a motor current waveform 424, a flow rate 426, a speed indicator 428, a contractility score 430 and a metric of state score 432. The pressure signal waveform 422 indicates the pressure measured by the blood pump's pressure sensor (e.g., pressure sensor 112). The pressure signal waveform 422 can be used by a healthcare professional to properly place an intravascular heart pump (such as intravascular heart pump 106 in FIG. 1) in the heart. The pressure signal waveform 422 may be used to verify the position of the intravascular heart pump by evaluating whether the waveform 422 is an aortic or ventricular waveform. An aortic waveform indicates that the intravascular heart pump motor is in the aorta. A ventricular waveform indicates that the intravascular heart pump motor has been inserted into the ventricle, which is the incorrect location. A scale 434 for the placement signal waveform is shown. The default scaling is 0-160 mmHg. It can be adjusted in 20 mmHg increments. To the right of the waveform is a display 433 that labels the waveform, provides the units of measurement, and shows the maximum and minimum values and the average value from the samples received.

The motor current waveform 424 is a measure of the energy intake of the heart pump's motor. The energy intake varies with the motor speed and the pressure difference between the inlet and outlet areas of the cannula resulting in a variable volume load on the rotor. When used with an intravascular heart pump (such as intravascular heart pump 106 in FIG. 1), the motor current provides information about the catheter position relative to the aortic valve. When the intravascular heart pump is positioned correctly, with the inlet area in the ventricle and the outlet area in the aorta, the motor current is pulsatile because the mass flow rate through the heart pump changes with the cardiac cycle. When the inlet and outlet areas are on the same side of the aortic valve, the motor current will be dampened or flat because the inlet and outlet of the pump are located in the same chamber and there is no variability in differential pressure resulting in a constant mass flow rate, and subsequently constant motor current. A scale 436 for the motor current waveform is displayed to the left of the waveform. The default scaling is 0-1000 mA. The scaling may be adjustable in 100 mA increments. To the right of the waveform is a display 425 that labels the waveform, provides the units of measurement, and shows the maximum and minimum values and the average value from the samples received.

The flow rate 426 can be a target flow rate set by the user or an estimated actual flow rate. In some modes of the controller, the controller will automatically adjust the motor speed in response to changes in afterload to maintain a target flow rate. In some implementations, if flow calculation is not possible, the controller will allow a user to set a fixed motor speed as indicated by speed indicator 428.

The contractility score 430 provides an indication of cardiac function. More specifically, the contractility score represents the inherent strength and vigor of the heart's contraction during systole. The stroke volume of the heart will be greater if the contractility of the heart is greater. For example, medium contractility may occur when the stroke volume of the heart is about 65 mL. High contractility may occur when the stroke volume of the heart is over 100 mL. Low contractility may occur when the stroke volume of the heart is less than 30 mL. The contractility score may be expressed numerically and/or graphically. The contractility score may be non-dimensional. Changes in contractility can be determined from the variation in slope of pressure during cardiac contraction (dP/dt). The metric of state score 432 also provides an indication of cardiac function. The metric of state score may be an indication of volume load, the pressure of a cardiac pressure, or another metric of cardiac function.

The position, depictions of the metrics on the controller, and the identification and number of metrics and recommendations in FIGS. 4A and 4B are meant to be illustrative. The number of metrics and indicators, position of same metrics and indicators on the console and the metrics displayed may be varied from those shown here. The metrics displayed to a user can include, but are not limited to, contractility, stroke volume, ejection fraction, chamber pressure, stroke work, cardiac output, cardiac power output, LVEDP, preload state, afterload state, flow load state, variable volume load state, cardiac cycle volume load state, cardiac cycle flow state, heart rate, and/or heart recovery as defined by any or all of the prior heart related parameters, the trends over time, and specific thresholds, or any other suitable metric derived from a hysteresis parameter associated with a cardiac assist device placed in or partially in an organ of a patient.

Some embodiments of the present disclosure relate to systems and methods for determining contractile reserve in a patient having a mechanical circulatory support device. As described herein, the motor current signal and/or the pressure signal associated with an intravascular heart pump system, such as the heart pump system 100 shown in FIG. 1, may be analyzed to determine one or more cardiac contractility metrics for a patient's heart. For instance, as shown in the user interface 400 of FIG. 4A, a cardiac state waveform 408 determined as a ratio of the contractility of the heart and the volume of blood pumped, may be displayed to show a recorded cardiac state of a patient over a period of time. Additionally, FIG. 4B shows a contractility score 430, which represents the inherent strength and vigor of the heart's contraction during systole. In accordance with some embodiments of the present disclosure, one or more cardiac contractility metrics (e.g., contractility index 308, contractility score 430) are measured at multiple performance levels (P-levels) of the mechanical circulatory support system to quantify the contractility metric at different pump performance states.

There are currently no known ways to measure contractile reserve in situ in either animal or human subjects. Rather, empirical titration of support and clinical judgment are typically used to determine how to wean a patient from a support device. The lack of standardized approaches and empirical evidence puts the patient at risk, as existing techniques require manual decrease of pump performance level exposing the patient to the risk of sudden hemodynamic collapse or compromise. The inventors have recognized and appreciated that by analyzing the variation of one or more cardiac contractility metrics at different pump performance levels (e.g., P-levels) corresponding to different motor speeds, a novel cardiac metric (referred to herein as a "contractile reserve metric") that provides a numeric assessment of the ability of the ventricle to adapt to changing levels of workload may be obtained. The contractile reserve metric may provide a physician with information relating to the ability of the heart to work independently of pump support, thus increasing patient safety while weaning the patient off of pump support or prior to and/or after attempting other pump adjustments.

Figure 5:
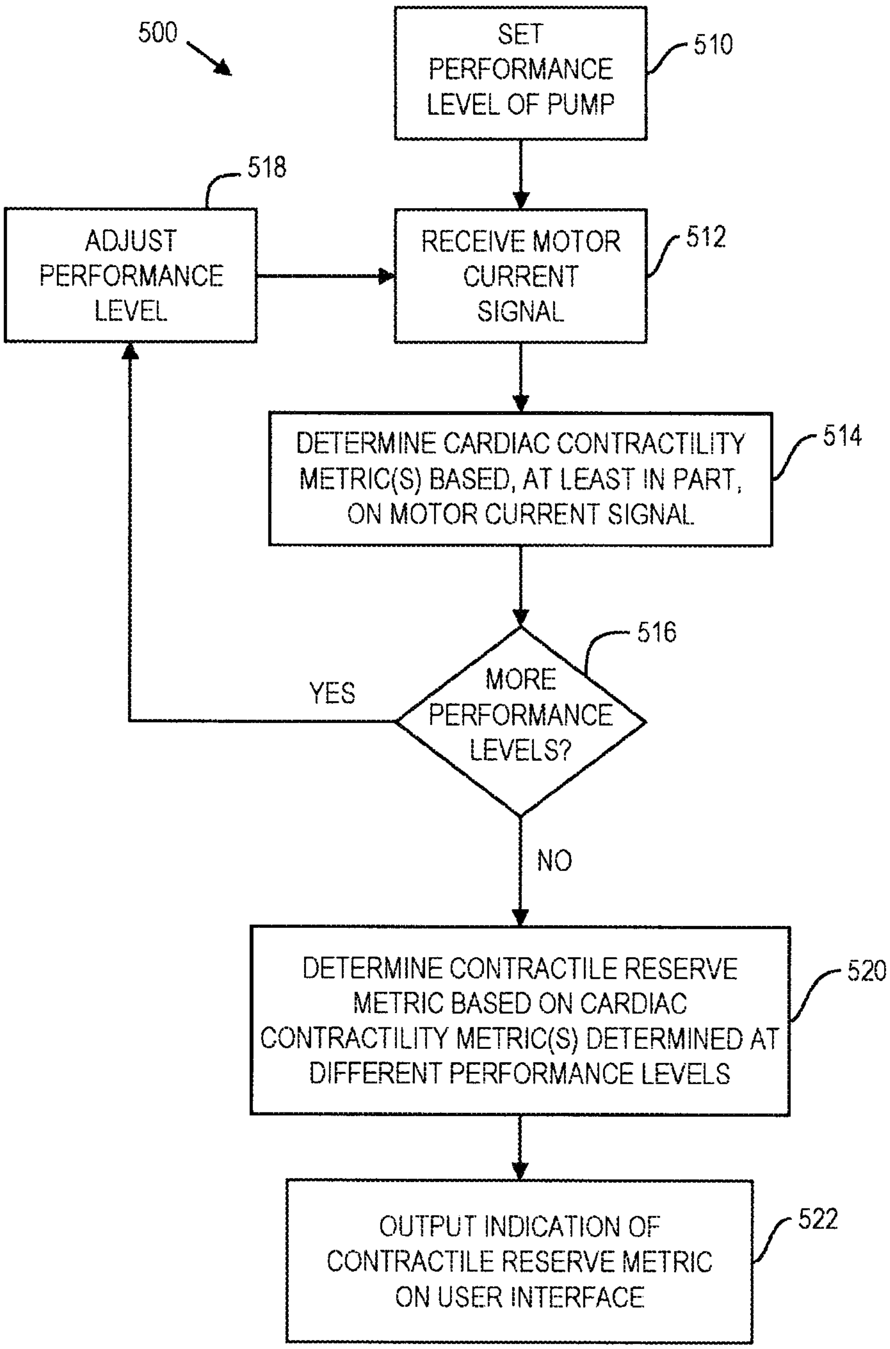
FIG. 5 is a flowchart of a process for determining a contractile reserve metric for a heart of a patient, in accordance with some embodiments of the present disclosure.

FIG. 5 is a flowchart of a process 500 for determining a contractile reserve metric based, at least in part, on a motor current signal associated with a motor of a mechanical circulatory support device (e.g., a heart pump device), in accordance with some embodiments of the present disclosure. In act 510, a performance level (e.g., a motor speed) of the heart pump device is set (e.g., using control system 104). Process 500 then proceeds to act 512, where a motor current signal is received, for example from one or more motor current sensors, as described in connection with heart pump system 100 shown in FIG. 1. Process 500 then proceeds to act 514, where one or more cardiac contractility metrics (e.g., contractility index 308, contractility score 430, etc.) are determined based, at least in part, on the motor current signal, in accordance with the techniques described herein. It should be appreciated that some cardiac contractility metrics may be determined based, at least in part, on information other than the motor current signal. For instance, one or more cardiac contractility metrics may be determined based, at least in part, on a pressure signal and/or data stored in a look-up table.

After determining the one or more cardiac contractility metrics for the set performance level of the pump in act 514, process 500 then proceeds to act 516, where it is determined whether there are additional performance levels of the heart pump system for which cardiac contractility metric(s) should be determined. As described herein, the inventors have recognized and appreciated that by determining cardiac contractility metric(s) at multiple pump performance levels, a contractile reserve metric for a patient's heart may be determined by examining the variability of the cardiac contractility metric(s) across the different performance levels. When it is determined in act 516 that there are additional pump performance levels for which the cardiac contractility metric(s) should be determined, process 500 proceeds to act 518, where the performance level of the pump is adjusted. Process 500 then returns to act 512 where the motor current signal determined when the pump is operating at the new pump performance level is received, and the motor current signal is used in act 514 to determine the one or more cardiac contractility metrics, as described herein. When it is determined in act 516 that there are no more additional pump performance levels for which the cardiac contractility metric(s) should be determined, process 500 proceeds to act 520, where a contractile reserve metric is determined based, at least in part, on the cardiac contractility metrics determined at the different performance levels of the heart pump.

In some implementations, the cardiac contractility metric(s) may be determined at each possible pump performance level at which the heart pump system is configured to operate. For instance, if the heart pump system is configured to operate at performance levels P1-P9, it may be determined in act 516 that additional performance levels exist until the cardiac contractility metric(s) have been determined for each of the nine pump performance levels. In other implementations, only a subset of the possible pump performance levels for a particular heart pump system may be used to determine a contractile reserve metric(s) in accordance with the techniques described herein. For instance, in some implementations, during the weaning process, the contractile reserve metric(s) may not be determined for higher pump performance levels of a heart pump system (i.e., faster motor speeds), as they may provide less relevant information about how the patient's native heart will function after the heart pump system is removed.

As shown in FIG. 5, in act 520, the contractile reserve metric may be determined based on the cardiac contractility metric(s) in various ways. For instance, the variability of the cardiac contractility metric(s) across the different pump performance levels may be analyzed to determine a numerical score for contractile reserve for the patient. Process 500 may then proceed to act 522, where an indication of the contractile reserve metric is provided on a user interface (e.g., user interface 400, user interface 401, etc.) associated with the heart pump system. The indication of the contractile reserve metric may be provided in any suitable way. For instance, a graph showing the contractile reserve metric plotted at different performance levels may be shown on the user interface. Additionally or alternatively, an indicator showing a numerical score associated with the contractile reserve metric at one or more performance levels, averaged across performance levels, etc. may be shown on the user interface.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The above-described embodiments of the present technology can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as a controller that controls the above-described function. A controller can be implemented in numerous ways, such as with dedicated hardware, or with general purpose hardware (e.g., one or more processor) that is programmed using microcode or software to perform the functions recited above, and may be implemented in a combination of ways when the controller corresponds to multiple components of a system.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles “a” and “an,” as used herein in the specification and in the claims, unless clearly indicated to the contrary, should be understood to mean “at least one.”

The phrase “and/or,” as used herein in the specification and in the claims, should be understood to mean “either or both” of the elements so conjoined, i.e., elements that are conjunctively present in some cases and disjunctively present in other cases. Multiple elements listed with “and/or” should be construed in the same fashion, i.e., “one or more” of the elements so conjoined. Other elements may optionally be present other than the elements specifically identified by the “and/or” clause, whether related or unrelated to those elements specifically identified. Thus, as a non-limiting example, a reference to “A and/or B”, when used in conjunction with open-ended language such as “comprising” can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase “at least one,” in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase “at least one” refers, whether related or unrelated to those elements specifically identified. Thus, as a non-limiting example, “at least one of A and B” (or, equivalently, “at least one of A or B,” or, equivalently “at least one of A and/or B”) can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of “including,” “comprising,” or “having,” “containing,” “involving,” and variations thereof herein, is meant to encompass the items listed thereafter and equivalents thereof as well as additional items.

In the claims, as well as in the specification above, all transitional phrases such as “comprising,” “including,” “carrying,” “having,” “containing,” “involving,” “holding,” “composed of,” and the like are to be understood to be open-ended, i.e., to mean including but not limited to. Only the transitional phrases “consisting of” and “consisting essentially of” shall be closed or semi-closed transitional phrases, respectively.

Use of ordinal terms such as “first,” “second,” “third,” etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The invention claimed is:

1. A method of assessing a contractile reserve of a heart of a patient, the heart of the patient having a mechanical circulatory support device arranged therein, the method comprising:

controlling the mechanical circulatory support device to operate at a first performance level associated with a baseline workload on the heart of the patient;

determining based, at least in part, on a motor current signal received from a motor when the mechanical circulatory support device is operating at the first performance level, at least one first value for a cardiac contractility metric;

controlling the mechanical circulatory support device to operate at a second performance level associated with an increased workload on the heart of the patient, the second performance level being lower than the first performance level;

determining based, at least in part, on the motor current signal received from the motor when the mechanical circulatory support device is operating at the second performance level, at least one second value for the cardiac contractility metric;

determining a contractile reserve metric based, at least in part, on the at least one first value and the at least one second value of the cardiac contractility metric, wherein the contractile reserve metric is indicative of an ability of the heart of the patient to adapt to the increased workload; and outputting an indication of the contractile reserve metric on a user interface associated with the mechanical circulatory support device.

2. The method of claim 1, wherein the mechanical circulatory support device is configured to operate at a predetermined number of performance levels including the first performance level and the second performance level, and wherein the method further comprises:

controlling the mechanical circulatory support device to operate at each of the predetermined number of performance levels; and determining based, at least in part, on the motor current signal received from the motor when the mechanical circulatory support device is operating at each of the predetermined number of performance levels, a corresponding at least one value for the cardiac contractility metric, wherein the contractile reserve metric is determined based, at least in part, on the at least one value determined when the mechanical circulatory support device was operating at each of the predetermined number of performance levels.

3. The method of claim 1, further comprising:

receiving, from a pressure sensor associated with the mechanical circulatory support device, a pressure signal, wherein the at least one first value for the cardiac contractility metric is determined based, at least in part, on the pressure signal when the mechanical circulatory support device was operating at the first performance level, and the at least one second value for the cardiac contractility metric is determined based, at least in part, on the pressure signal when the mechanical circulatory support device was operating at the second performance level.

4. The method of claim 1, wherein the at least one first value for the cardiac contractility metric and/or the at least one second value for the cardiac contractility metric is determined based, at least in part, on data stored in data storage associated with the mechanical circulatory support device.

5. The method of claim 1, wherein determining a contractile reserve metric based, at least in part, on the at least one first value for the cardiac contractility metric and the at least one second value for the cardiac contractility metric comprises analyzing a variance between the at least one first value for the cardiac contractility metric and the at least one second value for the cardiac contractility metric.

6. The method of claim 1, wherein outputting an indication of the contractile reserve metric comprises displaying on the user interface, a graph of the at least one value for the cardiac contractility metric determined at each of the first and second performance levels.

7. The method of claim 1, wherein outputting an indication of the contractile reserve metric comprises displaying on the user interface, a numerical value for the contractile reserve metric.

8. The method of claim 1, further comprising:

controlling the mechanical circulatory support device to operate at a third performance level, the third performance level being higher than the first performance level and/or the second performance level;

determining based, at least in part, on the motor current signal received from the motor when the mechanical circulatory support device is operating at the third performance level, at least one third value for the cardiac contractility metric; and determining the contractile reserve metric based, at least in part, on the at least one third value of the cardiac contractility metric.

9. A mechanical circulatory support device configured to be implanted in a heart of a patient, comprising:

a rotor;

a motor configured to drive rotation of the rotor at a plurality of speeds; and at least one controller configured to:

control the motor to operate at a first speed associated with a baseline workload on the heart of the patient;

determine based, at least in part, on a motor current signal received from the motor when operating at the first speed, at least one first value for a cardiac contractility metric;

control the motor to operate at a second speed associated with an increased workload on the heart of the patient, the second speed being lower than the first speed;

determine based, at least in part, on a motor current signal received from the motor when operating at the second speed, at least one second value for the cardiac contractility metric;

determine a contractile reserve metric based, at least in part, on the at least one first value for the cardiac contractility metric and the at least one second value for the cardiac contractility metric, wherein the contractile reserve metric is indicative of an ability of the heart of the patient to adapt to the increased workload; and output an indication of the contractile reserve metric on a user interface associated with the mechanical circulatory support device.

10. The mechanical circulatory support device of claim 9, wherein the at least one controller is further configured to:

control the motor to operate at a predetermined number of speeds including the first speed and the second speed; and determine based, at least in part, on the motor current signal received from the motor when the motor is operating at each of the predetermined number of speeds, a corresponding at least one value for the cardiac contractility metric, wherein the contractile reserve metric is determined based, at least in part, on the at least one value determined when the motor was operating at each of the predetermined number of speeds.

11. The mechanical circulatory support device of claim 9, further comprising:

a pressure sensor configured to measure a pressure signal, wherein the at least one first value for the cardiac contractility metric is determined based, at least in part, on the pressure signal when the motor was operating at the first speed, and the at least one second value for the cardiac contractility metric is determined based, at least in part, on the pressure signal when the motor was operating at the second speed.

12. The mechanical circulatory support device of claim 9, further comprising data storage, wherein the at least one first value for the cardiac contractility metric and/or the at least one second value for the cardiac contractility metric is determined based, at least in part, on data stored in the data storage.

13. The mechanical circulatory support device of claim 9, wherein determining a contractile reserve metric based, at least in part, on the at least one first value for the cardiac contractility metric and the at least one second value for the cardiac contractility metric comprises analyzing a variance between the at least one first value for the cardiac contractility metric and the at least one second value for the cardiac contractility metric.

14. The mechanical circulatory support device of claim 9, wherein the cardiac contractility metric includes a contractility index and/or a contractility score.

15. The mechanical circulatory support device of claim 9, wherein outputting an indication of the contractile reserve metric comprises displaying on the user interface, a graph of the at least one value for the cardiac contractility metric determined at each of the first and second speeds.

16. The mechanical circulatory support device of claim 9, wherein outputting an indication of the contractile reserve metric comprises displaying on the user interface, a numerical value for the contractile reserve metric.

17. A controller for a mechanical circulatory support device, the mechanical circulatory support device configured to be implanted in a heart of a patient, the controller comprising:

at least one hardware processor configured to:

control a motor of the mechanical circulatory support device to operate at a first speed associated with a baseline workload on the heart of the patient;

determine based, at least in part, on a motor current signal received from the motor when operating at the first speed, at least one value for a cardiac contractility metric;

control the motor to operate at a second speed associated with an increased workload on the heart of the patient, the second speed being lower than the first speed;

determine based, at least in part, on a motor current signal received from the motor when operating at the second speed, at least one second value for the cardiac contractility metric;

determine a contractile reserve metric based, at least in part, on the at least one first value for the cardiac contractility metric and the at least one second value for the cardiac contractility metric, wherein the contractile reserve metric is indicative of an ability of the heart of the patient to adapt to the increased workload; and output an indication of the contractile reserve metric on a user interface associated with the mechanical circulatory support device.

18. The controller of claim 17, wherein the at least one hardware processor is further configured to:

control the motor to operate at a predetermined number of speeds including the first speed and the second speed; and determine based, at least in part, on the motor current signal received from the motor when the motor is operating at each of the predetermined number of speeds, a corresponding at least one value for the cardiac contractility metric, wherein the contractile reserve metric is determined based, at least in part, on the at least one value determined when the motor was operating at each of the predetermined number of speeds.

19. The controller of claim 17, wherein the at least one hardware processor is further configured to:

receive, from a pressure sensor associated with the mechanical circulatory support device, a pressure signal, wherein the at least one first value for the cardiac contractility metric is determined based, at least in part, on the pressure signal when the motor was operating at the first speed, and the at least one second value for the cardiac contractility metric is determined based, at least in part, on the pressure signal when the motor was operating at the second speed.

20. The controller of claim 17, wherein determining a contractile reserve metric based, at least in part, on the at least one first value for the cardiac contractility metric and the at least one second value for the cardiac contractility metric comprises analyzing a variance between the at least one first value for the cardiac contractility metric and the at least one second value for the cardiac contractility metric.

* * * * *